(12) United States Patent
Doi et al.

(10) Patent No.: US 8,409,624 B2
(45) Date of Patent: Apr. 2, 2013

(54) ARTIFICIAL CEREBROSPINAL FLUID

(75) Inventors: Kazuhisa Doi, Naruto (JP); Yujiro Morioka, Itano-gun (JP); Takeshi Kawano, Naruto (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 728 days.

(21) Appl. No.: 11/911,828

(22) PCT Filed: Apr. 12, 2006

(86) PCT No.: PCT/JP2006/307736
§ 371 (c)(1),
(2), (4) Date: Oct. 18, 2007

(87) PCT Pub. No.: WO2006/115057
PCT Pub. Date: Nov. 2, 2006

(65) Prior Publication Data
US 2009/0092681 A1    Apr. 9, 2009

(30) Foreign Application Priority Data
Apr. 19, 2005  (JP) ................................. 2005-120476

(51) Int. Cl.
*A61K 35/30*    (2006.01)
(52) U.S. Cl. ........................ 424/570; 514/870
(58) Field of Classification Search .................. 514/870; 424/570
See application file for complete search history.

(56) References Cited

U.S. PATENT DOCUMENTS

| | | | | | |
|---|---|---|---|---|---|
| 5,071,536 | A | * | 12/1991 | Ivory | ............................ 204/549 |
| 5,200,200 | A | * | 4/1993 | Veech | ........................... 424/663 |
| 6,500,809 | B1 | * | 12/2002 | Frazer | ............................. 514/54 |
| 2006/0154873 | A1 | | 7/2006 | Sumiyoshi et al. | |

FOREIGN PATENT DOCUMENTS

| | | | |
|---|---|---|---|
| FR | 2439017 | A * | 6/1980 |
| JP | 10-323183 | A | 12/1998 |
| JP | 2000-308669 | A | 11/2000 |
| JP | 2002-173422 | A | 6/2002 |
| JP | 2005-500260 | A | 1/2005 |
| WO | 97/48365 | A1 | 12/1997 |
| WO | 02/078745 | A2 | 10/2002 |
| WO | 2004/108059 | A1 | 12/2004 |

OTHER PUBLICATIONS

Lewis et al., "Clinical Uses of an Artificial Cerebrospinal Fluid", 1950, Journal of Neurosurgery, vol. 7 iss. 3pp. 256-260.*
Oka et al., "The Significance of Artificial Cerebrospinal Fluid as Perfusate and Endoneurosurgery", Neurosurgery, vol. 38 Issue 4, abstract.*
Enomoto et al., Involvement of histone phosphorylation in apoptosis of human astrocytes after exposure to saline solution, Oct. 28, 2003, Neurochemistry International, vol. 44, pp. 459-467.*
Stanimirovic et al., Inflammatory Mediators of Cerebral Endothelium: A Role in Ischemic Brain Inflammation, 2000, Brain Pathology, vol. 10, pp. 113-126.*
Doi et al., Various irrigation fluids affect postoperative brain edema and cellular damage during experimental neurosurgery in rats, 2006, Surgical Neurology, vol. 66, pp. 565-572.*
Kazunari Oka, et al., "The Significance of Artificial Cerebrospinal Fluid as Perfusate and Endoneurosurgery," Neurosurgery, 1996, pp. 733-736, vol. 38, No. 4.
Ian Kenneth Pople, et al., "The Role of Endoscopic Choroid Plexus Coagulation in the Management of Hydrocephalus," Neurosurgery, 1995, pp. 698-702, vol. 36, No. 4.
C. Jin Whang, et al., "Successful Treatment of Ventriculitis by Continuous Intraventricular Irrigation with Gentamicin Solution," Surg. Neurol., 1974, pp. 91-94, vol. 2.
Theodore Rasmussen, et al., "Cortisone in the Treatment of Postoperative Cerebral Edema." J. Neurosurg., 1962, pp. 535-544, vol. 19, No. 7.
K. A. C. Elliott, et al., Physiological Salt Solutions for Brain Surgery, J. Neurosurg., 1949, pp. 140-152, vol. 6.
Korean Office Action dated Jul. 28, 2009 for corresponding Korean Patent Application No. 10-2007-7025501.
Koichi Uchida, et al., "Possible Harmful Effects on Central Nervous System Cells in the Use of Physiological Saline as an Irrigant During Neurosurgical Procedures," Surg Neurol, vol. 62, pp. 96-105, 2004.

* cited by examiner

*Primary Examiner* — Ali Soroush
(74) *Attorney, Agent, or Firm* — Sughrue Mion, PLLC (57) ABSTRACT

The present invention provides an artificial cerebrospinal fluid containing 120 to 160 mEq/L of sodium ion, 1 to 6 mEq/L of potassium ion, 75 to 155 mEq/L of chloride ion, and 5 to 45 mEq/L of bicarbonate ion, and provides an artificial cerebrospinal fluid further containing at least one component selected from the group consisting of 10 g/L or less of a reducing sugar, 5 mmol/L or less of phosphoric acid, 5 mEq/L or less of calcium ion, and 5 mEq/L or less of magnesium ion. The artificial cerebrospinal fluid of the present invention can prevent or reduce the incidence of cerebral edema and can further suppress brain cell disorders when used as an irrigation fluid or perfusion fluid in the field of neurosurgery, such as intracranial surgery, or when used as a replenishing fluid for lost cerebrospinal fluid.

1 Claim, 2 Drawing Sheets

ARTIFICIAL CEREBROSPINAL FLUID

TECHNICAL FIELD

The present invention relates to an artificial cerebrospinal fluid, particularly used in the fields of intracranial surgery and neurosurgery for the purpose of irrigation or perfusion, or replenishing lost cerebrospinal fluid, a packaged container holding the artificial cerebrospinal fluid, a method for reducing cerebral edema incidence using the artificial cerebrospinal fluid, and a method for inhibiting incidence of brain cell disorders using the artificial cerebrospinal fluid.

BACKGROUND ART

Normal saline solution, lactated Ringer's solution, etc., have been conventionally used as artificial cerebrospinal fluids for the purpose of replenishing cerebrospinal fluid (CSF) that is lost during neurosurgery. These artificial cerebrospinal fluids have also been used for irrigating and perfusing an operation site (intracerebroventricular irrigation or perfusion fluid) (see Non-Patent Documents 1 to 3). However, in cases where normal saline has been used for the above purpose, side effects such as headache, fever, cervical stiffness, etc., have been reported. Fever has also been reported with the use of other artificial cerebrospinal fluids.

Cerebral edema is known as a primary factor for higher post-operative morbidity or mortality in many intracranial surgeries (see Non-patent Document 4). For example, Elliott K. A. C. et al. conducted experiments using Solution A which contains sodium ion, potassium ion, calcium ion, magnesium ion, chloride ion, glucose, etc., and further a predetermined amount of bicarbonate ion, and Solution B which contains the same components as Solution A excluding bicarbonate ion, as irrigation fluids, respectively, and consequently suggested that the composition of the fluids is one of the factors associated with the development of cerebral edema after brain exposure in cats (see Non-Patent Document 5).

More specifically, Elliott reported that when the brain surfaces of cats were irrigated with Solution B and Solution A, significant vasodilation of the brain surface was observed with Solution A unlike with Solution B, and the pH of the brain surface was lowered with Solution A, whereas physiological pH was maintained with Solution B. Based on these findings, Elliott indicates the importance of the bicarbonate ion in the above irrigation fluid. However, Elliott does not suggest the composition of an irrigation fluid that can reduce the incidence of cerebral edema.

As described above, the irrigation fluid or perfusion fluid used in the neurosurgery presumably increase or have possibilities of increasing the incidence of post-operative cerebral edema. However, the relations between a composition of such irrigation fluid or perfusion fluid and cerebral edema have not been elucidated, and an irrigation fluid or perfusion fluid which can prevent cerebral edema from developing or reduce the incidence of the same has not yet been reported.

Non-Patent Document 1: Oka K. et al., "The significance of artificial cerebrospinal fluid as perfusate and endoneurosurgery", Neurosurgery, 38: 733-736, 1996

Non-Patent Document 2: Pople I. K. et al., "The role of endoscopic choroid plexus coagulation in the management of hydrocephalus", Neurosurgery, 36: 698-702, 1995

Non-Patent Document 3: Whang C. J. et al., "Successful treatment of ventricultis by continuous intraventricular irrigation with gentamicin solution", Surg. Neurol., 2: 91-94, 1974

Non-Patent Document 4: Rasmussen T. et al., "Cortisone in the treatment of postoperative cerebral edema", J. Neurosurg., 19: 535-544, 1962

Non-Patent Document 5: Elliott, K. A. C. et al., "Physiological salt solutions for brain surgery", J. Neurosurg., 6: 140-152, 1949

DISCLOSURE OF THE INVENTION

Problems to be Solved by the Invention

The present invention has been accomplished in view of the current state of the foregoing prior art. The primary object of the invention is to provide an artificial cerebrospinal fluid having a novel composition and being highly useful as an irrigation fluid or perfusion fluid capable of preventing cerebral edema, which is likely to occur when an artificial cerebrospinal fluid is used as an irrigation fluid or perfusion fluid in the field of brain neurosurgery such as intracranial surgery, from developing or capable of reducing the incidence of the same.

Means for Solving the Problem

The present inventors conducted extensive research to achieve the above object. As a result, they have found the following findings: when an artificial cerebrospinal fluid, comprising an aqueous solution containing a predetermined amount of specific electrolytic ions as shown below, and further containing as necessary a predetermined amount of other electrolytic ions, phosphoric acid, and reducing sugar, is used as an irrigation fluid or perfusion fluid in the intracranial surgery, heretofore unknown actions, i.e., an inhibitory action on post-operative cerebrovascular hyperpermeability and an inhibitory action on brain cell disorders are exhibited, thereby significantly reducing the risk of cerebral edema incidence and further inhibiting the incidence of brain cell disorders. The present invention is accomplished as a result of further studies based on these findings.

More specifically, the present application is to provide the inventions as described under each Item below.

Item 1. An artificial cerebrospinal fluid comprising an aqueous solution containing electrolytic ions in the following ranges:
120 to 160 mEq/L of sodium ion,
1 to 6 mEq/L of potassium ion,
75 to 155 mEq/L of chloride ion, and
5 to 45 mEq/L of bicarbonate ion.

Item 2. The artificial cerebrospinal fluid of Item 1, further comprising at least one component selected from the group consisting of 10 g/L or less of a reducing sugar, 5 mmol/L or less of phosphoric acid, 5 mEq/L or less of calcium ion, and 5 mEq/L or less of magnesium ion.

Item 3. The artificial cerebrospinal fluid of Item 1, wherein pH is in a range from 6.8 to 8.2.

Item 4. The artificial cerebrospinal fluid of Item 1, the fluid being an irrigation fluid or perfusion fluid for the intracranium or the cerebrospinal cavity, or a fluid replenisher for lost cerebrospinal fluid.

Item 5. The artificial cerebrospinal fluid of Item 1, the fluid being an agent for reducing post-operative cerebral edema incidence.

Item 6. The artificial cerebrospinal fluid of Item 1, the fluid being an inhibitor of brain cell disorders.

Item 7. A packaged container holding the artificial cerebrospinal fluid of Item 1, the container being made of a gas-permeable plastic and having at least two intercommunicable chambers therein, bicarbonate ion being held in a different chamber from a chamber holding calcium ion and magnesium ion, the container being enclosed in a gas-barrier packaging member, a carbon dioxide atmosphere being established in a space between the container and the packaging member.

Item 8. The packaged container of Item 7, wherein the container holds the artificial cerebrospinal fluid free of organic acids.

Item 9. The packaged container of Item 7, wherein the container further holds a reducing sugar in a different chamber from the chamber holding bicarbonate ion.

Item 10. The packaged container of Item 7, further comprising a pH-indicating device in a space between the container and the packaging member, the pH-indicating device detecting a carbon dioxide concentration in the space and undergoing a change in color in response to a change in the concentration.

Item 11. A method for reducing cerebral edema incidence in brain surgery, the method comprising irrigating or perfusing the intracranium or the cerebrospinal cavity of a brain surgery patient, using the agent for reducing post-operative cerebral edema incidence of Item 5, or replenishing lost cerebrospinal fluid of a brain surgery patient using the agent for reducing post-operative cerebral edema incidence of Item 5.

Item 12. A method for inhibiting incidence of brain cell disorders in brain surgery, the method comprising irrigating or perfusing the intracranium or the cerebrospinal cavity of a brain surgery patient, using the inhibitor of brain cell disorders of Item 6, or replenishing lost cerebrospinal fluid of a brain surgery patient using the inhibitor of brain cell disorders of Item 6.

The artificial cerebrospinal fluid and the packaged container holding the fluid of the invention are described in detail below.

(1) The Artificial Cerebrospinal Fluid of the Invention

The artificial cerebrospinal fluid of the present invention comprises an aqueous solution containing electrolytic ions in the following ranges:

| | |
|---|---|
| Sodium ion | 120 to 160 mEq/L, |
| Potassium ion | 1 to 6 mEq/L, |
| Chloride ion | 75 to 155 mEq/L, and |
| Bicarbonate ion | 5 to 45 mEq/L. |

When the aqueous solution having the specific composition as described above is used as an irrigation fluid or a perfusion fluid in the field of neurosurgery such as intracranial surgery, etc., the risk of post-operative cerebral edema incidence can be significantly reduced. Further, the aqueous solution exhibits an effect in inhibiting various brain cell disorders such as ion exchange disorder in brain cells. It is a totally novel finding that such effects can be attained by the use of an artificial cerebrospinal fluid having the above specific composition.

The artificial cerebrospinal fluid of the invention may further contain at least one component selected from the group consisting of 10 g/L or less of a reducing sugar, 5 mmol/L or less of phosphoric acid, 5 mEq/L or less of calcium ion, and 5 mEq/L or less of magnesium ion. These components may be contained singly or two or more may be contained together.

Among the components described above, it is presumed that a reducing sugar, phosphoric acid, calcium ion, magnesium ion, etc., are effective in maintaining electrical activity of brain neurons; a reducing sugar is also useful as an energy source for cells; and phosphoric acid, calcium ion and magnesium ion are useful for cell energy metabolism. It is further presumed that calcium ion is vital ion for the excitability and transmissibility of cells, and maintaining cell functions; and magnesium ion is effective ion for the activation of various intracellular enzymes.

To bring out these effects, it is preferable that a reducing sugar be contained in about 0.1 to about 10 g/L, phosphoric acid be contained in about 0.1 to about 5 mmol/L, calcium ion be contained in about 0.5 to about 5 mEq/L, and magnesium ion be contained in about 0.5 to about 5 mEq/L.

A preferable example of each component content in the artificial cerebrospinal fluid of the invention is as follows.

| | |
|---|---|
| Sodium ion | 120 to 160 mEq/L, |
| Potassium ion | 1 to 6 mEq/L, |
| Calcium ion | 1 to 5 mEq/L, |
| Magnesium ion | 1 to 5 mEq/L |
| Chloride ion | 75 to 155 mEq/L, |
| Bicarbonate ion | 5 to 45 mEq/L, |
| Phosphoric acid | 0 to 5 mmol/L, and |
| Reducing sugar | 0 to 10 g/L. |

Further, a more preferable example of each component content in the artificial cerebrospinal fluid of the invention is as follows.

| | |
|---|---|
| Sodium ion | 130 to 160 mEq/L, |
| Potassium ion | 1 to 4 mEq/L, |
| Calcium ion | 1 to 4 mEq/L, |
| Magnesium ion | 1 to 4 mEq/L |
| Chloride ion | 100 to 150 mEq/L, |
| Bicarbonate ion | 10 to 40 mEq/L, |
| Phosphoric acid | 0 to 3 mmol/L, and |
| Reducing sugar | 0 to 5 g/L. |

The following are examples of sources for these electrolytic ions (compounds for providing electrolytic ions). More specifically, examples of sodium ion sources include sodium chloride, sodium acetate, sodium citrate, sodium dihydrogenphosphate, disodium hydrogenphosphate, sodium sulfate, sodium lactate, etc.; examples of potassium ion sources include potassium chloride, potassium acetate, potassium citrate, potassium dihydrogenphosphate, dipotassium hydrogenphosphate, potassium glycerophosphate, potassium sulfate, potassium lactate, etc.; examples of calcium ion sources include calcium chloride, calcium gluconate, calcium pantothenate, calcium lactate, calcium acetate, etc.; examples of magnesium ion sources include magnesium sulfate, magnesium chloride, magnesium acetate, etc.; examples of chloride ion sources include sodium chloride, potassium chloride, calcium chloride, magnesium chloride, etc. Sodium bicarbonate (sodium hydrogencarbonate) can be typically used as a bicarbonate-ion source, but sodium carbonate can also be used as the source. As a phosphoric acid source, not only phosphoric acid ($H_3PO_4$) itself but a salt thereof, for example, monopotassium phosphate, dipotassium phosphate, monosodium phosphate, disodium phosphate, etc., can also be used. Glucose, maltose, etc. are used as reducing sugars. Usable as such electrolytic-ion-providing compounds, phosphoric acids, and reducing sugars are commercial products which can be easily obtained, and preferably products listed in Japanese Pharmacopoeia Reference Standards.

The compounds as electrolytic ion sources described above are typically used in the anhydride form (NaCl, KCl, $NaHCO_3$, $CaCl_2$, $MgCl_2$, etc.), but are not limited thereto, and can also be used in a form having crystal water, i.e., hydrate, such as $CaCl_2.2H_2O$, $MgCl_2.6H_2O$, $MgSO_4.7H_2O$, etc. The content of these hydrates in the artificial cerebrospinal fluid of the invention is different from that of anhydride; however, the content, regardless of the form, may suitably be selected so that the electrolytic ion concentration in the artificial cerebrospinal fluid obtained by mixing these sources is within the range described above.

The artificial cerebrospinal fluid of the invention has the above components dissolved in water. The water to be used for the preparation of the artificial cerebrospinal fluid may be purified water (ion exchanged water, reverse osmosis water, etc.), distilled water, etc. The water is preferably disinfected or sterilized.

The artificial cerebrospinal fluid having the composition described above typically has a pH of from about 6.8 to 8.2, more preferably from about 7 to 7.5, and can be used as an artificial cerebrospinal fluid as is. If necessary, the pH can be further adjusted using a suitable pH-adjusting agent, for example, acids such as hydrochloric acid and alkalis such as sodium hydroxide.

The artificial cerebrospinal fluid of the invention may further suitably contain, as necessary, other electrolytic components such as potassium acetate, calcium gluconate, etc.; other saccharides such as maltose, xlytol, trehalose, etc.; other components such as minute amounts of metals including copper, zinc, etc.; pharmaceutical components such as carnitine, etc. Furthermore, the artificial cerebrospinal fluid of the invention can contain thrombolytic agents such as glutathione, ketone bodies, urokinase, etc.; antibiotics such as gentamicin sulfate, amikacin sulfate, etc.; anticancer agents such as methotrexate (MTX), etc.; pharmaceutical components such as ascorbic acid, etc.

(2) Packaged Container Holding the Artificial Cerebrospianl Fluid of the Invention In view of preventing the formation of precipitates and coloration due to the decomposition of the reducing sugar contained, it is preferable that the artificial cerebrospinal fluid having the above composition be divided into at least two portions, held in separate containers, and the internal fluid in each container be mixed before use.

The artificial cerebrospinal fluid of the invention contains, as an essential component, bicarbonate ion which partially decomposes in the course of the sterilization and storage of the fluid and releases carbon dioxide gas, thereby disadvantageously causing the decomposition loss and pH rise of the fluid. Therefore, the preferable embodiment of the product holding the artificial cerebrospinal fluid of the invention is that which is able to avoid carbon dioxide gas generation and prevent pH rise in the fluid.

An example of the preferable product embodiment (embodiment for enclosing the container) for holding the artificial cerebrospinal fluid of the invention is a package in which a gas-permeable plastic container having at least two intercommunicable chambers is enclosed in a gas-barrier packaging member, with a carbon dioxide atmosphere established in a space between the container and the packaging member.

In such an embodiment of the packaged multiple-chamber container having at least two chambers, a solution containing bicarbonate ions (Solution A) is, for example, held in a chamber (Chamber A) of the above container, an electrolyte solution containing calcium ion and magnesium ion (Solution B) added as necessary is held in an another chamber (Chamber B), and a reducing sugar added as necessary is further held in the chamber holding the above electrolyte solution (Solution B), or in a third chamber (Chamber C) separate from the foregoing two chambers. When the solutions in the chambers are mixed before use, the mixture attains the composition of the artificial cerebrospinal fluid of the invention. A phosphoric acid added as necessary may preferably be held, for example, in the chamber holding the solution containing bicarbonate ion.

The concentration of each component and volume ratio in the internal chamber solutions are not limited insofar as the fluid prepared by mixing the solutions consequently has the above composition. A representative method for preparing the above form is as follows. Namely, sodium bicarbonate is dissolved in water for injection to prepare Solution A. Sodium chloride and/or potassium chloride may further be dissolved in Solution A. Calcium chloride, magnesium chloride, and, if necessary, a reducing sugar are dissolved in water for injection to prepare Solution B. Sodium chloride and/or potassium chloride may further be dissolved in Solution B. Subsequently, the thus obtained internal chamber solutions are filtered using, for example, a membrane filter having a pore size of 0.45 μm, and held in each chamber of the gas-permeable plastic container described above. Chloride ion may be present in Solution A and/or Solution B.

When using the above packaged multiple-chamber container having at least 2 chambers, the occurrence of precipitation due to the formation of a hardly soluble bicarbonate from calcium ion and/or magnesium ion with bicarbonate ion can be prevented by holding the bicarbonate-ion-containing solution in a chamber separate from the chamber where the calcium ion and/or magnesium ion are held. By virtue of this aspect, the prevention of precipitation occurrence over an extended period is enabled without adding an organic acid such as citric acid which is added to a conventional artificial cerebrospinal fluid as a chelating agent to prevent the formation of insoluble salts.

The above gas-permeable plastic container having at least two chambers may be any known one. Specific examples thereof include those equipped with closure means for a communicable part between the two chambers (Japanese Examined Patent Publication No. 1988-20550 and Japanese Examined Utility Model Publication No. 1988-17474), those in which a sealing part zoning two chambers is easily communicable by pressing (Japanese Unexamined Patent Publications Nos. 1988-309263 and 1990-4671), etc. Examples of materials for the above container include a wide range of materials typically used for medical containers such as polyethylene, polypropylene, polyvinyl chloride, cross-linked vinylacetate-alcohol, etc. The container may be made of a mixture of resins of these materials, or a laminate composed of resin films of these materials. The thus obtained container is desired to be particularly resistant to high-pressure steam sterilization or hydrothermal sterilization.

The packaged container for holding the artificial cerebrospinal fluid of the invention is produced by enclosing the above gas-permeable plastic container in a gas-barrier packaging member, and establishing a carbon-dioxide-containing gas atmosphere in the space between the container and the packaging member.

The gas-barrier packaging member may be any of those typically used, and specific examples include polyethylene terephthalate (PET), ethylene vinylalcohol copolymer (EVOH), polyvinylidene chloride (PVDC), those having a vapor-deposition layer of silicon oxide or aluminium oxide on these materials, those consisting of multilayer films made from combinations of these materials, etc. The shape and size of these packaging members are not limited so long as they are able to enclose the above plastic container, leaving enough space between the container and the packaging member to accept a carbon dioxide-containing gas after packaging. The suitable volume of the above space is about 0.1 to about 0.8 times the volume of the solution in the container.

To establish a carbon dioxide-containing gas atmosphere in the space between the above container and the packaging member, for example, a method for enclosing a carbon-dioxide-containing gas such as a mixed gas of carbon dioxide gas and air, a mixed gas of carbon dioxide gas and nitrogen gas, etc., in the space described above can be employed. Alternatively employable is a method that encloses in the above space a carbon-dioxide-gas-generating oxygen absorber, which absorbs oxygen gas present in the space and releases carbon dioxide gas equal to the volume of oxygen gas absorbed. Examples of advantageously usable carbon-dioxide-gas-generating oxygen absorbers include "Ageless G", product of Mitsubishi Gas Chemical Company, and Keep Fresh Type C, product of Toppan Printing Co., Ltd., etc.

By the employment of the above structure, the carbon dioxide gas present in the space between the container and the packaging member passes through the wall of the gas-permeable plastic container and is absorbed into Solution A, and the partial pressure of the carbon dioxide gas in Solution A equilibrates with the partial pressure of the carbon dioxide gas in the space, whereby the carbon dioxide gas acts as a pH-adjusting agent of Solution A.

The packaged container for holding the artificial cerebrospinal fluid of the invention preferably has within the space between the container and the packaging member a pH-indicating device (including those termed pinhole detectors), which detects the carbon dioxide gas concentration in the space and undergoes a change in color in response to a concentration change of the carbon dioxide gas.

The pH-indicating device herein may be any of those that undergo a change in color in response to a change of a carbon dioxide gas concentration in the above space. Examples include those containing a carbonate-containing solution and a pH-indicating agent in a packet, etc. Specific examples thereof are as described in detail in, e.g., WO97/48365.

The pH-indicating agent to be added to the above internal solution of the pH-indicating device may be selected from a variety of acid-base indicators capable of indicating a pH change of the internal solution of the device as a color change. In particular, a preferable example is a pH-indicating agent that sensitively undergoes a change in color (discoloration) in around the pH region of the above internal solution of the pH-indicating device at the equilibrium carbon dioxide gas concentration in the space that corresponds to the pH at which the validity of the bicarbonate ion-containing solution is impaired (the upper limit value according to Japanese Pharamcopoeia Standards for the product) by releasing carbon dioxide gas from the bicarbonate ion-containing solution due to, for example, an accident such as a pinhole formation in the packaging member. Generally, the pH at which the validity of a bicarbonate ion-containing solution is impaired is on the alkaline side (e.g., the standardized upper limit for a 7% aqueous solution of sodium bicarbonate is pH 8.6 according to Japanese Pharmacopoeia XIII, and the corresponding carbon dioxide gas concentration is about 19%). Since the pH of the internal solution of the pH-indicating device, which is proportional to the pH of the bicarbonate ion-containing solution, is also on the alkaline side (e.g., the pH of a 0.28% aqueous solution of sodium bicarbonate is 7.0), the pH-indicating agent described above is preferably a substance that undergoes a change in color on the weak alkaline side.

Particularly preferable pH-indicating agents have properties as follows; (1) a narrow color change area, (2) high color intensity, (3) suitable direction of color change (from indistinctive to distinctive colors), (4) outstanding hygiene (the agent itself is highly safe and not migratory), and (5) good stability with the initial color change property being sustained for an extended time. In the present invention, a pH-indicating agent having these properties is desirably used. Preferable examples of such pH-indicating agent include neutral red, aurin, phenol red, o-cresol red, α-naphtholphthalein, m-cresol purple, orange I, phenolphthalein, etc., with phenol red (change from yellow to red at pH 6.8 to 8.4 or higher), o-cresol red (change from yellow to red at pH 7.2 to 8.8 or higher), and m-cresol purple (change from yellow to purple at pH 7.6 to 9.2 or higher) being suitable.

The concentration of the above pH-indicating agent may be any concentration as long as any changes in color are easily recognized with the naked eye, and the concentration is preferably selected from a range from, for example, about 10 to about 2000 ppm, depending on the size (thickness of the liquid layer) of the packet in which the agent is enclosed together with the internal indicating device solution.

The packet enclosing the above internal solution and the pH-indicating agent can be produced by a known method. A material for the gas-permeable plastic container to be used for the packet may be those having gas-permeability (air-permeability) equal to or higher than materials for the container holding the artificial fluid described above. The above packet can be fabricated, for example, in a continuous series of forming, filling and sealing by means of a vertical 3-side sealer, a vertical pillow packaging machine, a rotary packer, or the like.

When the above manufacturing method is employed, the material for the packet is preferably a laminated film in consideration of machine processability. Particularly, when a polyethylene container is used for the container holding the artificial cerebrospinal fluid, a polypropylene (outer layer)-polyethylene (inner layer) laminate film or a poly-4-methyl-1-pentene (outer layer)-polyethylene (inner layer) laminate film are preferred.

Regarding the size of the packet and the volume of the internal solution, if the amount of the internal solution enclosed in the packet is too small, the thickness of the indicating device solution layer will be too thin, whereby a visual judgment with the naked eye of the color change is likely to be difficult. For this reason, the packet size and the internal solution volume should be suitably determined in consideration of the ease at judgment of the color change with the naked eye as well as the sizes of the artificial cerebrospinal fluid holding container and the packaging member.

The pH-indicating device thus prepared may develop turbidity owing to bacterial growth in the internal solution during prolonged storage. To prevent or control this problem, it can be sterilized by high-pressure steam sterilization. Alternatively, an antiseptic such as benzalkonium chloride, chlorohexidine gluconate, etc., an antibacterial agent such as nalidixic acid, norfloxacin, etc., and/or a preservative such as p-hydroxybenzoic esters, benzyl alcohol, etc., may be added as necessary.

The packet is disposed in the space simply by packaging the artificial cerebrospinal fluid holding container and the packet together in the packaging member. The position at which the packet is disposed is not limited insofar as it may be visually recognized from outside even after being packaged in the packaging member. In this manner, an improved package allowing a visual inspection with the naked eye of the pH change of the artificial cerebrospinal fluid can be obtained.

In the packaged container for holding the artificial cerebrospinal fluid having the above structure, an ink composition for carbon dioxide gas concentration detection containing a pH-indicating agent, binder (thickener) and solvent may be used as a pH-indicating device. When an indication area for carbon dioxide gas concentration detection using such an ink composition is provided in the space between the container for holding the artificial cerebrospinal fluid and the packaging member, a visual inspection with the naked eye of the pH change of the artificial cerebrospinal fluid is enabled as in the case of employing a pH-indicating device which contains a carbonate-containing solution and a pH-indicating agent in a packet. The ink composition can be utilized for forming the indication area for carbon dioxide gas concentration detection by a variety of methods such as a method in which a plastic film on which the ink composition is applied is disposed in the space, a method in which the ink composition is applied on the inner surface of the packaging member, a method in which the ink composition is applied on the outer surface of the artificial cerebrospinal fluid holding container, etc. Specific examples of such ink compositions for carbon dioxide gas concentration detection and the applications thereof are as described in detail in WO01/44385 pamphlet, etc.

In the invention, the procedures for filling the artificial cerebrospinal fluid into the container (each chamber in the container), sterilizing the fluid, packaging the container with the packaging member as well as establishing a carbon dioxide atmosphere within the space are the same as those typically employed for manufacturing injectable solutions, and are hence easily carried out.

Figure 1:
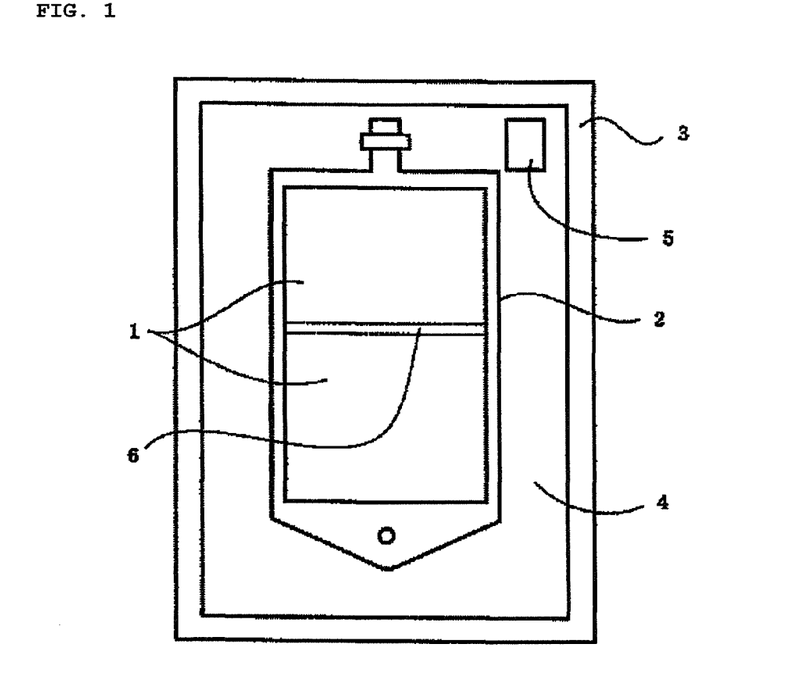
FIG. 1 is a schematic view showing a preferred embodiment of the packaged container for holding the artificial cerebrospinal fluid of the present invention.

A preferable embodiment of the packaged container for holding the artificial cerebrospinal fluid according to the invention is as shown in an attached drawing (FIG. 1). The package comprises a gas-permeable plastic container 2 having two chambers partitioned by an intercommunicable sealing member 6, and a gas-barrier packaging member 3 enclosing the container, with a carbon dioxide atmosphere established in the space 4 between the container and the packaging member where a pH-indicating device 5 is disposed. Each chamber of the above container 2 holds liquid solution 1, which attains the composition of the artificial cerebrospinal fluid of the invention when admixed.

Having the above structure, the packaged product of the invention can assure the following advantages: it is not easily breakable, adaptable for increased capacity, and has a reduced weight due to the use of a plastic container; problems such as the occurrence of precipitation and coloration are reliably avoided due to the container having two chambers; dissipation of carbon dioxide gas released from the artificial cerebrospinal fluid (a bicarbonate ion-containing solution) is prevented due to the employment of the gas-barrier packaging member and establishment of a carbon dioxide atmosphere within; and consequent maintenance of the solution pH at a constant range is attained. Further, the packaged container holding the artificial cerebrospinal fluid of the invention in which the pH-indicating device described earlier is disposed offers easy judgment with the naked eye of the pH change and the degradation of the fluid caused by problems such as prolonged storage or formation of a pinhole in the packaging member. Furthermore, the packaged product of the invention has the advantage of being easily fabricated by conventional manufacturing techniques in any of the above embodiments.

Moreover, the artificial cerebrospinal fluid of the invention may be stored in a medical solution container made of a material to which a gas-barrier property is imparted. Such a medical solution container made of a gas-barrier material may be a container formed of a multi-layered plastic film including a gas-barrier layer. Examples of medical solution containers having such a structure are those disclosed in Japanese Unexamined Patent Publications Nos. 2002-234102 and 1993-8318, etc. A specific example of a usable container is formed of a multi-layered film wherein an inner layer and an outer layer respectively made of gas-permeable polyethylene film and polypropylene film, with ethylene vinylalcohol copolymer (EVOH), a gas-barrier film, interposed therebetween. The gas-barrier film preferably used is a transparent film so as to enable the visual assessment of the medical solution. The medical solution container to which the gas-barrier properties are imparted may be a container having at least two intercommunicable chambers.

Another embodiment of the gas-barrier medical solution container is a container having a structure in which both surfaces of the gas-permeable plastic film constituting the container are covered by gas-barrier films. In this embodiment, when the medical solution container made of a gas-permeable plastic film consists of two chambers, for example, only the chamber where a bicarbonate ion-containing solution (Solution A) is contained may be covered with a gas-barrier film. The barrier film is preferably a transparent film so that the medical solution can be visually observed. Examples of such medical solution containers are described in Japanese Unexamined Patent Publications Nos. 1999-276547 and 2003-267451, Japanese Registered Utility Model No. 3112358, etc.

When the artificial cerebrospinal fluid of the invention is stored in a gas-barrier medical solution container, an indication area for carbon dioxide gas concentration detection may be provided at an opening portion of the container body using the aforementioned ink composition for carbon dioxide gas detection containing a pH-indicating agent, binder (thickener), and solvent. For example, the container can have a structure wherein the opening portion of the container body is sealed using a gas-permeable sealer, whose outside is detachably sealed by a gas-barrier covering member, and a gas detector is disposed between the covering member and the gas-permeable sealer. Owing to this structure, in the case that the sealing performance of the medical solution container is impaired, it is easily detected from outside. Specific examples of methods for disposing the gas detector include a method wherein the above ink composition is applied to the inner surface of a gas-barrier covering member formed on the outside the gas-permeable sealer, a method wherein the ink composition is thus applied, followed by adhesion of a protective film thereon, etc. The medical solution container provided with an indication area for carbon dioxide gas concentration detection at the opening portion thereof is as described in, e.g., Japanese Unexamined Patent Publication No. 2005-349182.

(3) Application of the Artificial Cerebrospinal Fluid of the Invention

The artificial cerebrospinal fluid of the present invention is used in accordance with known procedures. For example, the artificial cerebrospinal fluid of the invention contained in the gas-permeable plastic container having at least two intercommunicable chambers can be practically used after the above two chambers are brought into intercommunication to admix (or dilute) the internal solutions of both chambers.

The artificial cerebrospinal fluid of the invention can be used as an irrigation fluid or perfusion fluid for the intracranium or the cerebrospinal cavity.

Specific aspects of this use are as follows.

1. Use in brain neurosurgery (craterization and craniotomy) as an irrigation fluid for the purpose of irrigating an operation site, eliminating the air from an operation site, cooling of tissues to dissipate the heat generated when operation instruments are used, and not affecting hemostasis.

2. Use in neuroendoscopic surgery as a perfusion fluid for assuring clear visibility, not affecting hemostasis, and having a texture that does not hinder surgical procedures.

3. Use as a perfusion fluid for eliminating the hematoma in cisternae perfusion therapy after subarachnoid hemorrhage.

The amount of the artificial cerebrospinal fluid of the invention to be used is not limited, and can be suitably selected in accordance with the purpose of use in the surgeries mentioned above. It is typically used at a maximum amount of about 4000 mL as a guide, and the amount can be increased based on the on-site judgment of a doctor during an actual operation. Usages of the fluid may be varied depending on the form of operation. Examples of suitable applications include the following: the fluid is directly dropped onto an operation site using a dropper or syringe; the fluid is sprayed (insufflated) to necessary areas such as an operation site; the fluid is perfused at a constant rate to necessary areas such as an operation site using a suitable tube or the like; a gauze, impregnated with the fluid, is placed on the brain surface to prevent the surface from drying, the fluid is dropped from an instrument such as coagulator, drill, when used; etc.

Further, the artificial cerebrospinal fluid of the invention can be used as a fluid replenisher for cerebrospinal fluid in case it is lost during brain surgery, etc.

As described above, the artificial cerebrospinal fluid of the invention can significantly reduce the risk of post-operative cerebral edema incidence when it is used as an irrigation fluid or perfusion fluid for the intracranium or the cerebrospinal cavity, or as a fluid replenisher for lost cerebrospinal fluid during brain neurosurgery, and is hence very useful in the neurosurgery field. This is demonstrated in Test Example 1 to be described later. The artificial cerebrospinal fluid of the invention when used as an intracerebral irrigation fluid during neurosurgery is indeed capable of notably reducing the risk of post-operative cerebral edema incidence in comparison with normal saline solution and lactated Ringer's solution.

The known factors of cerebral edema are post-operative cerebrovascular hyperpermeability and ion exchange disorders in the brain cell membrane. The artificial cerebrospinal fluid of the invention has both an inhibitory action on post-operative cerebrovascular hyperpermeability and an inhibitory action on brain cell disorders, and is hence able to remarkably reduce the risk of cerebral edema incidence. Further, the artificial cerebrospinal fluid of the invention is also effective in suppressing, in addition to the ion exchange disorders in brain cells which is possible risk factors for cerebral edema, other brain cell disorders, which are likely to adversely affect other brain functions and the living body, for example, disorders of glial cells such as neurons, astrocytes, etc.

Consequently, the artificial cerebrospinal fluid of the invention is useful as an agent for the reduction of the incidence of post-operative cerebral edema, and is further useful as an inhibitor of brain cell disorders.

Furthermore, the artificial cerebrospinal fluid of the invention can also be used, for example, as an entoptic perfusion fluid.

The present inventors performed safety tests on the artificial cerebrospinal fluid of the invention, and assured that the fluid has higher safety due to the specific composition thereof than that of normal saline solution and lactated Ringer's solution. Based also on this finding, the artificial cerebrospinal fluid of the invention has properties for mitigating a risk of a patient during a neurosurgery operation, and is hence advantageous in the neurosurgery field.

EXPLANATION OF REFERENCE NUMBERS

1 Artificial cerebrospinal fluid of the invention
2 Gas-permeable plastic multiple-chamber container
3 Gas-barrier packaging member
4 Space between the gas-permeable plastic multiple-chamber container 2 and gas-barrier packaging member 3
5 pH-indicating device
6 Intercommunicable seal portion

BEST MODE FOR CARRYING OUT THE INVENTION

The present invention is described below in reference to TEST EXAMPLES and EXAMPLES, but is not limited thereto.

Example 1

Each component, shown under the titles Upper Chamber Solution and Lower Chamber Solution in Table 1 below, was weighed, and mixed and dissolved in distilled water for injection respectively, thereby preparing 150 mL of the upper chamber solution and 350 mL of the lower chamber solution.

A lower chamber (a chamber equipped with a solution outlet connecting to a port portion, illustrated in the upper part of FIG. 1) of a container 2 (made of polyethylene) of the packaged container for holding the artificial cerebrospinal fluid as shown in FIG. 1 was filled with the thus obtained lower chamber solution from the solution outlet, and the outlet was tightly sealed. Similarly, the upper chamber (a chamber separated from the above lower chamber by a partitioning wall, the chamber adjoining to a suspension portion, illustrated in the lower part of the figure) before being tightly sealed was filled with the obtained upper chamber solution, and then hermetically sealed.

TABLE 1

| Components | Amount (g) |
| --- | --- |
| Upper Chamber Solution (per 150 mL) | |
| Calcium Chloride • dihydrate | 0.085 |
| Magnesium Chloride • hexahydrate | 0.110 |
| Glucose | 0.305 |
| Lower Chamber Solution (per 350 mL) | |
| Sodium Bicarbonate | 0.970 |
| Potassium Dihydrogenphosphate | 0.075 |
| Sodium Chloride | 3.575 |
| Potassium Chloride | 0.065 |

The obtained container was subjected to high-pressure steam sterilization, dehydrated, and packaged in a gas-barrier film (Bovlon Film, product of The Nippon Synthetic Chemical Industry Co., Ltd., a biaxially oriented polyvinyl alcohol film, thickness: 14 μm), together with a pH-indicating device (the device disclosed in Production Example 5 of Japanese Unexamined Patent Publication No. 1999-197215). When packaging was performed, about 400 ml of a mixed gas of 18% carbon dioxide-air was filled in the space between the container and the packaging member. A packaged container holding the artificial cerebrospinal fluid of the invention was thus obtained.

The packaged container holding the artificial cerebrospinal fluid of the invention produced above was allowed to stand indoors for a week, and opened. The partitioning wall in the container was opened to admix the internal container solutions. The thus obtained mixed solution was measured for concentrations of electrolytic ions as well as phosphoric acid and glucose in accordance with the Liquid Chromatography guidance under General Tests in the Japanese Pharmacopoeia. The pH value of the solution was also determined in accordance with the pH Determination guidance under General Tests in the Japanese Pharmacopoeia. Table 2 shows the results.

TABLE 2

| Components | Amount |
| --- | --- |
| $Na^+$ | 145.4 mEq/L |
| $K^+$ | 2.8 mEq/L |
| $Ca^{2+}$ | 2.3 mEq/L |
| $Mg^{2+}$ | 2.2 mEq/L |
| $Cl^-$ | 128.5 mEq/L |
| $HCO_3^-$ | 23.1 mEq/L |
| Phosphoric Acid | 1.1 mmol/L |
| Glucose | 0.61 g/L |
| Solution pH | 7.3 |

Example 2

Another packaged container holding the artificial cerebrospinal fluid of the invention was produced in the same manner as in EXAMPLE 1, except that glucose was not included in the upper chamber solution described in EXAMPLE 1, and the same measurements were performed. The results obtained are shown in Table 3 below.

TABLE 3

| Components | Amount |
| --- | --- |
| $Na^+$ | 145.4 mEq/L |
| $K^+$ | 2.8 mEq/L |
| $Ca^{2+}$ | 2.3 mEq/L |
| $Mg^{2+}$ | 2.2 mEq/L |
| $Cl^-$ | 128.5 mEq/L |
| $HCO_3^-$ | 23.1 mEq/L |
| Phosphoric Acid | 1.1 mmol/L |
| Glucose | 0.61 g/L |
| Solution pH | 7.3 |

Example 3

Another packaged container holding the artificial cerebrospinal fluid of the invention was produced in the same manner as in EXAMPLE 1, except that potassium dihydrogenphosphate was not included in the lower chamber solution described in EXAMPLE 1, and the same measurements were performed. The results obtained are shown in Table 4 below.

TABLE 4

| Components | Amount |
| --- | --- |
| $Na^+$ | 145.4 mEq/L |
| $K^+$ | 1.7 mEq/L |
| $Ca^{2+}$ | 2.3 mEq/L |
| $Mg^{2+}$ | 2.2 mEq/L |
| $Cl^-$ | 128.5 mEq/L |
| $HCO_3^-$ | 23.1 mEq/L |
| Glucose | 0.61 g/L |
| Solution pH | 7.3 |

Example 4

Each component shown in Table 5 below was weighed, and mixed and dissolved in distilled water for injection to prepare 500 ml of an aqueous solution.

A single-chamber polyethylene container having a solution outlet was filled with the obtained aqueous solution via the solution outlet, which was then tightly sealed.

TABLE 5

| Components | Amount (g) |
| --- | --- |
| Glucose | 0.305 |
| Sodium Bicarbonate | 0.970 |
| Potassium Dihydrogenphosphate | 0.075 |
| Sodium Chloride | 3.575 |
| Potassium Chloride | 0.065 |

Subsequently, the obtained container was subjected to high-pressure steam sterilization and dehydrated in the same manner as in EXAMPLE 1, and packaged in a gas-barrier film together with a pH-indicating device. About 400 ml of a mixed gas of 18% carbon dioxide-air was filled in the space between the container and the packaging member. Thus, a packaged container holding the artificial cerebrospinal fluid of the invention was obtained.

The packaged container holding the artificial cerebrospinal fluid of the invention obtained above was allowed to stand indoors for a week, and opened. The internal container solution was measured for concentrations of electrolytic ions as well as phosphoric acid and glucose in accordance with the Liquid Chromatography guidance under General Tests in the Japanese Pharmacopoeia. The pH value of the internal solution was also determined in accordance with the pH Determination guidance under General Tests in the Japanese Pharmacopoeia. Table 6 below shows the results.

TABLE 6

| Components | Amount |
| --- | --- |
| $Na^+$ | 145.4 mEq/L |
| $K^+$ | 2.8 mEq/L |
| $Cl^-$ | 126.3 mEq/L |
| $HCO_3^-$ | 23.1 mEq/L |
| Phosphoric Acid | 1.1 mmol/L |
| Glucose | 0.61 g/L |
| Solution pH | 7.3 |

Example 5

A packaged container holding the artificial cerebrospinal fluid of the invention was prepared in the same manner as in EXAMPLE 4, except that glucose and potassium dihydrogenphosphate were excluded from the components used in EXAMPLE 4.

The obtained packaged container holding the artificial cerebrospinal fluid was allowed to stand indoors for a week, and the internal fluid was measured for concentrations of each component in the same manner as in EXAMPLE 4. The results are shown in Table 7 below.

TABLE 7

| Components | Amount |
|---|---|
| $Na^+$ | 145.4 mEq/L |
| $K^+$ | 2.8 mEq/L |
| $Cl^-$ | 126.3 mEq/L |
| $HCO_3^-$ | 23.1 mEq/L |
| Solution pH | 7.3 |

Test Example 1

This test is to study effectiveness of the artificial cerebrospinal fluid of the invention when used as a brain irrigation fluid of a rat model for experimental post-operative cerebral edema, and was carried out as follows.

(1) Materials

The irrigation fluid sample used was the artificial cerebrospinal fluid according to the invention prepared in the same manner as in EXAMPLE 1 and having the composition shown in Table 8 below (test group). The artificial cerebrospinal fluid of the invention used herein can be used by breaking a partitioning wall separating these two chambers from each other and mixing a bicarbonate-ion-containing solution held in a chamber (lower chamber) of the plastic bag having two intercommunicable chambers as shown in FIG. 1 with a solution containing each electrolyte and glucose held in the other chamber (upper chamber). Table 9 shows the concentration of each component after mixed, and the pH of the mixed solution.

TABLE 8

| Components | Amount (g) |
|---|---|
| Upper Chamber Solution (per 150 mL) | |
| Sodium Chloride | 1.200 |
| Calcium Chloride • dihydrate | 0.085 |
| Magnesium Chloride • hexahydrate | 0.110 |
| Glucose | 0.305 |
| Lower Chamber Solution (per 350 mL) | |
| Sodium Bicarbonate | 0.970 |
| Potassium Dihydrogenphosphate | 0.075 |
| Sodium Chloride | 2.375 |
| Potassium Chloride | 0.065 |

TABLE 9

| Components | Amount |
|---|---|
| $Na^+$ | 145.4 mEq/L |
| $K^+$ | 2.8 mEq/L |
| $Ca^{2+}$ | 2.3 mEq/L |
| $Mg^{2+}$ | 2.2 mEq/L |
| $Cl^-$ | 128.5 mEq/L |
| $HCO_3^-$ | 23.1 mEq/L |
| Phosphoric Acid | 1.1 mmol/L |
| Glucose | 0.61 g/L |
| Solution pH | 7.3 |

For comparison, normal saline solution and lactated Ringer's solution (Normal Saline Group and Lactated Ringer Group) were used. The normal saline solution used was "Otsuka Normal Saline" ($Na^+$ 154 mEq/L and $Cl^-$ 154 mEq/L), product of Otsuka Pharmaceutical Factory, Inc. The lactated Ringer's solution used was "Lactec injection (registered trademark)" ($Na^+$ 130 mEq/L, $K^+$ 4 mEq/L, $Ca^{2+}$ 3 mEq/L, $Cl^-$ 109 mEq/L, lactate$^-$ 28 mEq/L), product of Otsuka Pharmaceutical Factory, Inc.

(2) Test Procedures

Twenty-four SD male rats of 7 to 9 weeks of age were used for the test. The rats were allowed free access to drinking water and food until the test was initiated. The rats were randomly divided into three groups, each consisting of 8 rats.

The rats in each group were anesthetized by intraperitoneal administration of 7 ml/kg (1.4 g/kg) of a 20 w/v % urethane solution, and the entire calvaria was shaved using a hair clipper. The rats were set in a brain stereotaxic apparatus (SR-6N, a product of Narishige Scientific Instrument Lab), the calvariae were disinfected with 70% alcohol, and an incision was made on the skin (initiation of surgery) to expose the cranial bone. A barrier, having a 1-mm height, made of a silicone tube (internal diameter 6 mm, external diameter 8 mm, a product of AS ONE Corporation) was bonded on the left parietal bone. Within the barrier, a bone window having about a 4-mm diameter was drilled (drill: MINITOR-7C-307M, product of Kanto Kiki Co., Ltd.) so that the center of the bone window was located 2.5 mm to the left from the midline and 4 mm posterior to the bregma.

As test samples, the artificial cerebrospinal fluid of the invention (present invention group, 8 rats), normal saline solution (normal saline group, 8 rats), and lactated Ringer's solution (Lactated Ringer group, 8 rats) were respectively infused into the bone window using a JMS syringe pump SP-100S (JMS Inc.) at 150 ml/hr, upon which irrigation was initiated. Subsequently, while irrigating, two incisions were made in a crisscross shape to a depth reaching the left cerebrocortex from the dura mater through the arachnoid membrane (depth 1.5 mm, length 3.5 mm) within the bone window using the edge of a blade (Feather Replacement Blade, stainless steel No. 25, Feather Safety Razor Co., Ltd.) attached to an electrode holder of a stereotaxic micromanipulator (SM-15, a product of Narishige Scientific Instrument Laboratory) to detach the dura mater and arachnoid membrane at the incision site (incision making). Clots formed within the bone window within 10 minutes of the incisions having been made were removed using a pair of tweezers. The irrigation was completed 4 hours after the incisions had been made. The body temperature (rectal temperature) of the model rats were maintained at about 37° C. using a feedback-controlled lamp and a warming pad (ATB-1100, a product of NIHON KOHDEN CORPORATION) until completion of the irrigation.

The rats of each group were then sacrificed by bleeding from the abdominal aorta, and the brain was quickly extirpated. The brain was temporarily isolated in ice-cold kerosene to prevent it from drying. Cerebral cortex tissue samples were collected from the intersection, along with the lines of the incisions made above, in a cubical shape having a length of about 0.5 mm and a depth of about 0.5 mm (tissues at the incision site).

According to the procedure of Marmarou et al. (J. Neurosurg., 1978 October; 49(4), pp. 530-537), specific gravity columns were made using bromobenzene and kerosene whose specific gravities are already known. Into the column were immersed the samples collected above, and the depths they had reached after 2 minutes were measured from which specific gravities (water contents) of the samples were determined based on calibration curves created beforehand. The specific gravity columns were calibrated using standard potassium sulfate solutions having a specific gravity of 1.020, 1.029, 1.038, 1.047, and 1.056, respectively, before use.

The specific gravity method, by which water content in a tissue is determined from the density of moist tissue using specific gravity columns as used in this test, is widely used in the study of cerebral edema. In this method, the lower a specific gravity is, the greater the water content is, thereby indicating more serious cerebal edema.

(3) Statistical Analysis

The test results are reported using the average±standard deviation of the results obtained from 8 rats of each group. Further, an intergroup comparison based on the results on evaluation of the tissues at the incision sites obtained from each group was conducted using Tukey's method at a 5% level of significance. In the Figures, "##" and "***" indicate $p<0.01$ and $p<0.001$, respectively.

(4) Results

Figure 2:
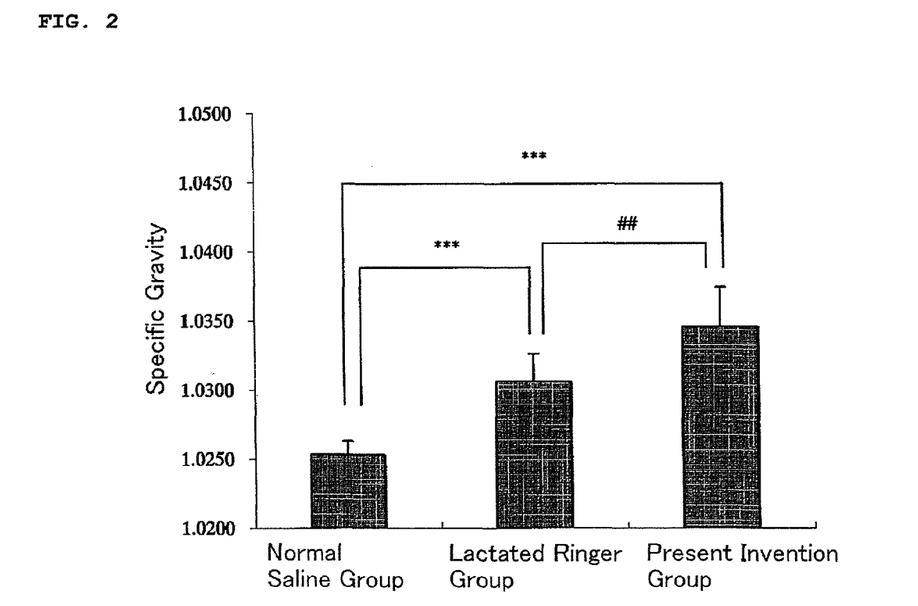
FIG. 2 is a graph showing the specific gravities of brain tissues at an incision site, calculated in accordance with TEST EXAMPLE 1 using each irrigation fluid.

The specific gravities determined for the brain tissues from the incision sites irrigated with each irrigation fluid sample are shown in FIG. 2 (vertical scale: specific gravity) for each irrigation fluid.

(5) Discussion

The results shown in FIG. 2 reveal that specific gravity at the incision site is the lowest in the Normal Saline Group, the second lowest in the Lactated Ringer Group, and the highest in the Present Invention Group. Based on this finding, the artificial cerebrospinal fluid of the invention evidently reduces the degree of experimental post-operative cerebral edema in comparison with normal saline solution and lactated Ringer's solution.

Test Example 2

Cerebral edema is classified into two types depending on the factors involved. One is vasogenic edema. In this type of edema, cerebrovascular hyperpermeability is caused by damage to the blood-brain barrier which consequently allows water to accumulate in the extra-cellular spaces of the brain while serum protein such as albumin leaks. The other is cytotoxic edema. In this type of edema, the ion exchange in the brain cell membrane is dysfunctional and causes intracellular water retention. Both types of edema are often seen together in actual cerebral edema cases.

Among these factors for cerebal edema, this test example is to examine the effects of the artificial cerebrospinal fluid of the invention on the permeability of cerebral blood vessels.

Serum proteins do not influx into the brain tissue under the normal conditions; however, when the brain is damaged, serum proteins pass through the damaged blood-brain barrier and enter into the extra-cellular spaces of the brain tissue (vascular hyperpermeability). Serum proteins, such as albumin, that have entered into the brain tissue trigger water inflow to the brain tissue due to osmotic pressure. Such an extravascular serum protein leakage associated with vascular hyperpermeability is thought to result in the formation of cerebral edema.

Evan's blue is known to bind to albumin in vivo, and, due to this property, is widely used for protein leakage assay as an index of vascular permeability. In this Test Example, the extravascular leakage of Evan's blue was assayed as an index of cerebrovascular permeability.

The test was carried out as follows.

(1) Materials

The artificial cerebrospinal fluid of the invention prepared in EXAMPLE 1 was used as an irrigation fluid sample (Test Group). For comparison, normal saline solution and lactated Ringer's solution (Normal Saline Group and Lactated Ringer Group) were also used. The compositions of these solutions are as shown in TEST EXAMPLE 1 above.

(2) Test Procedures (2-1) Brain Incision, Incision Site Irrigation and Evan's Blue Administration Twenty-four SD male rats of 7 to 9 weeks of age were used for the test. The rats were allowed free access to drinking water and food until the test was initiated. The rats were randomly divided into three groups, each consisting of 8 rats.

The rats in each group were anesthetized under intraperitoneal administration of 7 ml/kg (1.4 g/kg) of a 20 w/v % urethane solution, and the entire calvaria was shaved using a hair clipper. The rats were set in a brain stereotaxic apparatus (SR-6N, product of Narishige Scientific Instrument Lab), the calvariae were disinfected with 70% alcohol, and an incision was made on the skin (initiation of surgery) to expose the cranial bone. A barrier, having a 1-mm height, made of a silicone tube (internal diameter 6 mm, external diameter 8 mm, product of AS ONE Corporation) was bonded on the left parietal bone. Within the barrier, a bone window having about a 4-mm diameter was drilled (drill: MINITOR-7C-307M, product of Kanto Kiki Co., Ltd.) so that the center of the bone window was located 2.5 mm to the left from the midline and 4 mm posterior to the bregma.

As test samples, the artificial cerebrospinal fluid (Present Invention Group, 8 rats), normal saline (Normal Saline Group, 8 rats), and lactated Ringer's solution (Lactated Ringer Group, 8 rats) were respectively infused into the bone window using a JMS syringe pump SP-100S (JMS Inc.) at 150 ml/hr, upon which irrigation was initiated. Subsequently, while irrigating, two incisions were made in a crisscross shape to a depth reaching the left cerebrocortex from the dura mater through the arachnoid membrane (depth 1.5 mm, length 3.5 mm) within the bone window with the edge of a blade (Feather Replacement Blade, stainless steel No. 25, Feather Safety Razor Co., Ltd.) attached to an electrode holder of a stereotaxic micromanipulator (SM-15, product of Narishige Scientific Instrument Laboratory) to detach the dura mater and arachnoid membrane at the incision site (incision making). The body temperatures (rectal temperature) of the model rats were maintained at about 37° C. using a feedback-controlled lamp and a warming pad (ATB-1100, product of NIHON KOHDEN CORPORATION) until completion of the irrigation.

Clots formed within the bone window within 10 minutes of the incisions having been made were removed using a pair of tweezers. Three hours after the incisions had been made, 5 ml/kg of a 2 w/v % Evans Blue-containing normal saline solution (which was prepared by dissolving 0.2 g of Evan's blue, (product of Wako Pure Chemical Industries, Ltd.) in normal saline solution (Otsuka Normal Saline, product of Otsuka Pharmaceutical Factory, Inc.) to give 10 ml) was administered via the tail vain. The irrigation of the incision site with the test samples was continued until 4 hours after the incision had been made.

(2-2) Preparation of Fluorescence Measurement Samples

Immediately after completion of irrigation with the samples, thoracotomy was performed on the rats of each group, 262 to 266 mL of a normal saline solution (Otsuka Normal Saline, a product of Otsuka Pharmaceutical Factory, Inc.) was infused into the left ventricle from a container set so that the bottom end thereof was located about 100 cm above the rat, and was perfused so as to be discharged with blood from the right ventricle, followed by taking out the brain.

Further, the left and right cerebral cortexes were separated, spread on a plate (biological sample trimming plate, product of Nisshin EM Corporation), and brain tissue samples at the incision site of the left cerebral cortex were collected using a cork borer (No. 1, a product of Nonaka Rikaki Seisakusho, Co., Ltd.).

After measurement of each tissue sample, 0.01 M phosphate buffer (which was prepared by diluting 0.1 M phosphate buffer ("hereinafter abbreviated as "PB") 10 times with water before use, the 0.1 M phosphate buffer being prepare by mixing 667 ml of water and Phosphate Buffer 5 (pH 7.4, product of Latron Ltd.)) in an amount 10 times the tissue sample weight (calculated taking the specific gravities of the cerebrum and 0.01 M phosphate buffer as 1) was added to each tissue sample, homogenized using a homogenizer (potter type, a product of AS ONE Corporation), and 50 w/v % TCA (which was prepared by diluting 100 w/v % trichloroacetate solution (Wako Pure Chemical Industries, Ltd.) with water to give 50 w/v %) in an amount 10 times the tissue sample weight was further added thereto, and then mixed for 2 minutes in a touch mixer. The mixture was moved to a microtube, allowed to stand at room temperature for 30 minutes, and centrifuged at 13000 rpm for 40 minutes at room temperature using a centrifuge (MX-300, rotor: TMA-300, rack: ARO15-24, products of TOMY SEIKO Co., Ltd.). The supernatant was collected, and diluted with ethanol in an amount 3 times that of the supernatant, thereby obtaining a diluted solution for use as a fluorescence measurement sample.

(2-3) Fluorescence Measurement

The fluorescence measurement of each sample was performed using a spectrofluorometer (FP-750, product of JASCO Corporation) under the following conditions.
Measurement Menu Fixed Wavelength Measurement
Excitation Wavelength (band width): 620 nm (10 nm)
Measurement Wavelength (band width): 680 nm (10 nm)
Response Time: 1 second
Sensitivity: Medium Zero adjustment (autozero) was calibrated using Diluent A (which was prepared by adding 0.01 M PB to an equivalent amount of 50 w/v % TCA and mixing, and further adding ethanol to the mixture in an amount 3 times the mixture before use), and standard solutions for the calibration curves and fluorescence measurement samples were filtered using DISMIC-13JP (0.2 μm, nonaqueous, a product of Advantec Toyo Kaisha, Ltd.). The fluorescence measurement was first performed on the filtrate of the standard solutions for the calibration curve, and then on the filtrate of the fluorescence measurement samples.

(2-4) Determination of Evan's Blue Concentration in Brain Tissues

The determination was carried out by the absolute calibration curve method with the fluorescence intensity at a measurement wavelength of 680 nm, using calculation software (Microsoft Excel (registered trademark), Microsoft Corporation). By measuring the calibration curve standard solution, calibration curve formula of the fluorescence intensity at the measurement wavelength was determined by the least square method. The correlation coefficient (r) of the calibration curve was 0.99 or higher. Based on the calibration curve formula, the Evan's blue concentration in the fluorescence measurement sample was determined. The Evan's blue concentration in the brain tissue was determined by multiplying the Evan's blue concentration in a fluorescence measurement sample by the dilution rate (84-fold, calculated taking the specific gravities of the brain and Diluent A as 1) with which fluorescence measurement samples were prepared from the brain tissue samples.

(3) Statistical Analysis

The test results were expressed using averages±standard deviation of the results obtained from 8 rats of each group. Further, an intergroup comparison based on the results on evaluation of the tissues at the incision sites obtained from each group were conducted using Tukey's method at a 5% level of significance. In the Figures, ** indicates <0.01.

(4) Results

Evan's Blue Concentrations in the Brain Tissues via Evan's Blue Stain Test

Figure 3:
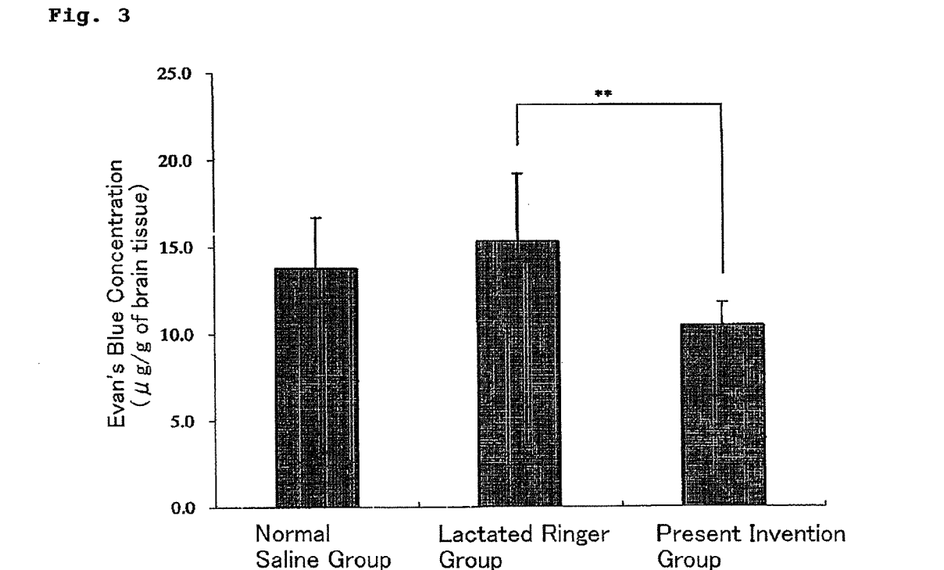
FIG. 3 is a graph showing the measurement results of Evan's Blue concentrations in brain tissues at an incision site of each rat group, obtained by testing in accordance with TEST EXAMPLE 2.

FIG. 3 shows the measurement results, expressed as averages±standard deviation, of the Evan's blue concentrations (μg/g of brain tissue) in the brain tissues at the incision sites for the rats of each group. The results shown in FIG. 3 reveal the following.

Specifically, the Evan's blue concentrations at the above incision sites (i.e., cerebrovascular hyperpermeability) in Present Invention Group were found to be significantly lower ($p<0.01$) than those of the Lactated Ringer Group, and tended to be lower than those of Normal Saline Group.

(5) Discussion

As a result of the Evan's blue assay in the brain tissue, the extravascular leakage of the Evan's blue in the Present Invention Group was significantly lower than that of the Lactated Ringer Group, and has a lower value when compared with the Normal Saline Group. These results reveal that the artificial cerebrospinal fluid of the present invention is able to effectively reduce the degree of cerebrovascular hyperpermeability, a primary factor of cerebral edema, in an experimental neurosurgery operation using rat models.

As described above, cerebrovascular hyperpermeability causes water to flow into the brain tissue from the inside of vessels and causes cerebral edema; however, the artificial cerebrospinal fluid of the invention hardly affects the cerebrovascular permeability, and is hence evidently not likely to cause post-operative cerebral edema. Considering that the brain-blood barrier has a control function on the transfer of various substances between the blood and brain tissues, the effect, which scarcely affects the above cerebrovascular permeability, attained by the use of the artificial cerebrospinal fluid of the invention further means that less damage is inflicted upon such a function. Based on these findings, the artificial cerebrospinal fluid of the present invention is thought to be useful as an almost ideal irrigation fluid to maintain the physiological condition of an intracerebral environment.

Test Example 3

Test Example 3 was to study the influence of the artificial cerebrospinal fluid of the present invention on brain cell disorders, one of the risk factors for cerebral edema.

2,3,5-Triphenyltetrazolium chloride (TTC) is converted to a red dye (formazan) by mitochondria enzymes present in viral cells. The degree of any brain cell disorders can be evaluated by dyeing the brain tissues with TTC and measuring the absorbance of the solvent in which formazan is extracted. More specifically, the lower the TTC stainability, the higher the degree of brain cell disorder is.

In this TEST EXAMPLE, incisions made in the brains of the rats, mimicking surgical brain incisions made during neurosurgery, were irrigated with each irrigation fluid, and the degrees of cell disorder were evaluated using the stainability of TTC in brain tissue as an index. The test procedures are as follows.

(1) Irrigation Fluid Samples

The irrigation fluid samples used were the artificial cerebrospinal fluid of the invention prepared in EXAMPLE 1 (Present Invention Group), and, for comparison, normal saline solution and lactated Ringer's solution (Normal Saline Group and Lactated Ringer Group, respectively). The compositions of these fluids were the same as those in TEST EXAMPLE 1 above.

(2) Test Procedures (2-1) Brain Incisions and Irrigation Thereof

Thirty-two SD male rats of 7 to 9 weeks of age were used for the test. The rats were allowed free access to drinking water and food until the test was initiated.

The rats were randomly divided into four groups, each consisting of 8 rats. Among these groups, the rats of three groups were categorized as the Present Invention Group (8 rats), the Normal Saline Group (8 rats), and the Lactated Ringer Group (8 rats), and incisions were made and the incision sites were irrigated with the samples in the same manner as in TEST EXAMPLE 2 above (provided that a 2 w/v % Evans Blue-containing normal saline solution was not administered).

The rats of the remaining one group (Control Group) were anesthetized upon intraperitoneal administration of 7 ml/kg of a 20 w/v % urethane solution, and the body temperature (rectal temperature) was maintained at about 37° C. using a feedback-controlled lamp and a warming pad (ATB-1100, a product of NIHON KOHDEN CORPORATION) for 4 hours.

(2-2) TTC Staining and Extraction

After completion of irrigating the incisions, the rats of the Present Invention Group, Normal Saline Group, and Lactated Ringer Group were quickly decapitated, and the heads were cooled with ice for about 30 seconds. The left and right cerebral cortexes were separated from the extirpated brain, spread on an ice-cooled plate (biological sample trimming plate, product of Nisshin EM Corporation), and brain tissue samples at the incision site of the left cerebral cortex and at the corresponding site (non-incision site) of the right cerebral cortex were collected using a cork borer having an internal diameter of about 4 mm (No. 1, product of Nonaka Rikaki Seisakusho, Co., Ltd.).

The equivalent tissue samples of the left and right cerebral cortexes were collected from the rats of Control Group.

Each brain tissue sample, divided into two parts in the middle, was placed in a vial, and measured for the weight at the time of the collection, 5 ml of a 2% TTC solution was then added thereto, and incubated in the shade at 37° C. for 90 minutes in a constant temperature bath equipped with a shaker (Personal-11SD, a product of TAITEC Corporation). The 2% TTC solution was removed, the samples were washed twice respectively with 5 ml of normal saline solution, and about 5 g of a solvent for formazan extraction (a mixture of an equivalent amount of ethanol and dimethylsulphoxide) was added to each vial, which was then hermetically sealed and allowed to stand in a dark place. After 24 hours, the formazan extraction solvent was recovered from the vial, and used as a sample for absorbance measurement.

(3) Measurement of TTC Stainability of Brain Tissue

The absorbance of the solvent used to extract formazan from the TTC-stained brain was measured at 485 nm, using an ultraviolet visible spectrophotometer (v-550, product of JASCO Corporation). The solvent for formazan extraction was taken as blank. The measured absorbances were corrected using the protein concentration of each brain tissue sample. Lowry's method was employed to determine the protein concentration in each brain tissue sample.

The TTC stainabilities of the brain tissues are indicated by the absorbance per mg of protein.

(4) Statistical Analysis

Mean and standard deviation (SD) values of the TTC stainability of the brain tissues were determined. Significance testing was performed using the following method.

More specifically, as to TTC stainabilities of the brain tissues at the incision sites of the rats, TTC stainabilities of the Present Invention Group, Lactated Ringer Group and Normal Saline Group were compared with that of Control Group, which were taken as the standard, using Dunnett's multiple comparison test. In case a significant difference was found in any group, the TTC stainabilities of Present Invention Group, taken as the standard, were compared with those of the Lactated Ringer Group and Normal Saline Group by Donnett's multiple comparison test. The non-incision sites were complementarily tested in the same manner. The significance level was 5%.

Data compilation was performed using calculation software (Microsoft Excel (registered trademark), product of Microsoft Corporation), and the statistical analysis software used was EXSAS Ver. 7.14 (product of Arm Systex Co., Ltd.).

(5) Results

Figure 4:
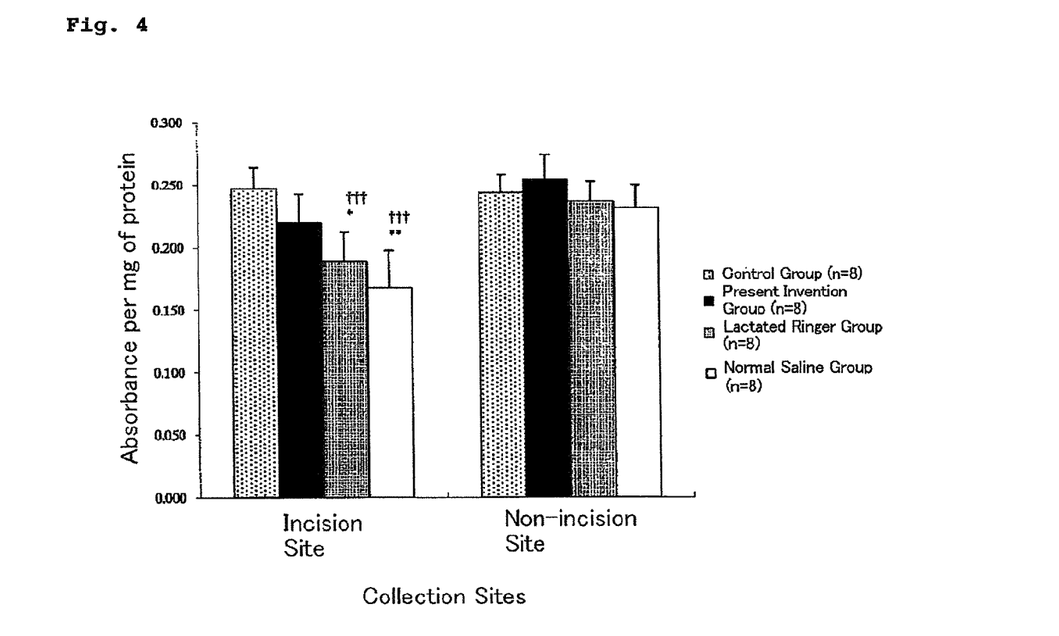
FIG. 4 is a graph showing absorbance per mg of protein at an incision site of each rat group, obtained by testing in accordance with TEST EXAMPLE 3.

FIG. 4 shows the TTC stainabilities (absorbance per mg of protein) of the brain tissues at the incision sites and non-incision sites of each group. The brain tissue TTC stainabilities at the incision sites (corresponding site on the left cerebral cortex in the Control Group) were $0.247 \pm 0.017$ in the Control Group, $0.220 \pm 0.023$ in the Present Invention Group, $0.189 \pm 0.023$ in the Lactated Ringer Group, and $0.168 \pm 0.030$ in the Normal Saline Group. The Lactated Ringer Group and Normal Saline Group exhibited statistically significantly lower values ($p<0.001$ in both groups) than the Control Group. The Lactated Ringer Group and Normal Saline Group also exhibited significantly lower values ($p<0.05$ and $p<0.01$, respectively) than the Present Invention Group.

The brain tissue TTC stainabilities of the non-incision sites were $0.244 \pm 0.014$ in the Control Group, $0.254 \pm 0.020$ in the Present Invention Group, $0.237 \pm 0.016$ in the Lactated Ringer Group, and $0.232 \pm 0.018$ in the Normal Saline Group, and no significant difference was found between the Control Group and the other groups.

(6) Discussion

As described above, the absorbance measurement of the solvent, which was used to extract formazan from the TTC stained brain tissues, can be used as an index of experimental brain damage. In this TEST EXAMPLE, the method of Preston et al. (Preston E, Webster J. Spectrophotometric Measurement of Experimental Brain Injury, J. Neurosci Methods. 2000; 94; 187-92) was partially modified, in that the TTC stainability per unit weight of the brain tissue sample was determined by correcting the absorbance of the solvent that was used to extract formazan with the protein content in the brain tissue sample, whereby the degrees of cell disorder were compared. According to this test method, it is shown that the lower the TTC stainability is, the higher the degree of cell disorder in the brain tissue is.

The TTC stainabilities at the incision sites in the Present Invention Group had slightly lower values than those of the Control Group; however, there was no significant difference between these groups. The TTC stainabilities at the incision sites in the Lactated Ringer Group and the Normal Saline Group were significantly lower than those of the Control Group, and cell disorders were demonstrated. Further, since the rats of the Lactated Ringer Group and the Normal Saline Group had significantly lower values than Present Invention Group, they are shown to have a higher degree of cell disorders than the rats in Present Invention Group.

Considering the above, the evaluation of cell disorder degree during irrigation of the incision site made on the cerebrum of the rats, using the TTC stainability as an index, demonstrated that cell disorders are milder when the incision site is irrigated with the artificial cerebrospinal fluid of the invention in comparison with the cases in which lactated Ringer's solution and normal saline solution were used for irrigation.

In TEST EXAMPLE 3, cell disorder degree was evaluated using mitochondria enzyme activity in brain cells as an index. It is presumed that when the function of the mitochondria enzymes decreases, the production of adenosine triphosphate (ATP) required to sustain cell membrane functions is reduced, whereby the ion exchange of the cell membrane is adversely affected. Given this, the results of TEST EXAMPLE 3 suggest that suppression of ion exchange disorder in cells can be achieved by irrigating an incision site with the artificial cerebrospinal fluid of the present invention.

The invention claimed is:

1. A method for reducing cerebral edema incidence in brain surgery, comprising the steps of:
   irrigating or perfusing the intracranium or the cerebrospinal cavity of a brain surgery patient with an artificial cerebrospinal fluid, or
   replenishing lost cerebrospinal fluid of a brain surgery patient with the artificial cerebrospinal fluid,
   wherein said irrigation, perfusion or replenishment reduces the incidence of cerebral edema in said patient,
   wherein the artificial cerebrospinal fluid consists of electrolytic ions in the following concentration ranges:
   120 to 160 mEq/L of sodium ion,
   1 to 6 mEq/L of potassium ion,
   75 to 155 mEq/L of chloride ion,
   5 to 45 mEq/L of bicarbonate ion,
   0.5 to 5 mEq/L of calcium ion,
   0.5 to 5 mEq/L of magnesium ion,
   0.1 to 5 mmol/L of phosphoric acid, and
   0.1 to 10 g/L of a reducing sugar, and
   wherein the artificial cerebrospinal fluid has a pH in a range from 6.8 to 8.2.

* * * * *